(12) United States Patent
Brennan et al.

(10) Patent No.: US 11,571,128 B2
(45) Date of Patent: Feb. 7, 2023

(54) FAST LABEL-FREE METHOD FOR MAPPING CARDIAC PHYSIOLOGY

(71) Applicant: The George Washington University, Washington, DC (US)

(72) Inventors: Jaclyn Brennan, Washington, DC (US); Igor R. Efimov, Arlington, VA (US)

(73) Assignee: The George Washington University, Washington, DC (US)

( * ) Notice: Subject to any disclaimer, the term of this patent is extended or adjusted under 35 U.S.C. 154(b) by 417 days.

(21) Appl. No.: 16/661,733

(22) Filed: Oct. 23, 2019

(65) Prior Publication Data

US 2020/0129071 A1  Apr. 30, 2020

Related U.S. Application Data

(60) Provisional application No. 62/749,937, filed on Oct. 24, 2018.

(51) Int. Cl.
| | | |
|---|---|---|
| *A61B 5/00* | (2006.01) | |
| *G01N 21/64* | (2006.01) | |
| *G01N 33/483* | (2006.01) | |
| *G01N 21/17* | (2006.01) | |

(52) U.S. Cl.
CPC ....... *A61B 5/0044* (2013.01); *G01N 21/6486* (2013.01); *G01N 33/4833* (2013.01); *A61B 5/0071* (2013.01); *A61B 5/743* (2013.01); *G01N 2021/1736* (2013.01)

(58) Field of Classification Search
CPC ... A61B 5/0044; A61B 5/0071; A61B 8/0883; G01N 21/6486; G01N 33/4833
See application file for complete search history.

(56) References Cited

U.S. PATENT DOCUMENTS

| | | |
|---|---|---|
| 5,769,846 A | 6/1998 | Edwards et al. |
| 2008/0306394 A1 | 12/2008 | Zdeblick |
| 2009/0143685 A1 | 6/2009 | Elner et al. |
| 2010/0087782 A1 | 4/2010 | Ghaffari |
| 2011/0224665 A1 | 9/2011 | Crosby |
| 2012/0157804 A1 | 6/2012 | Rogers et al. |
| 2014/0058197 A1 | 2/2014 | Salahieh |
| 2014/0088442 A1 | 3/2014 | Soykan |
| 2015/0141767 A1 | 5/2015 | Rogers et al. |
| 2015/0141847 A1 | 5/2015 | Saivazyan |
| 2015/0196208 A1 | 7/2015 | Dvorsky et al. |
| 2017/0319068 A1 | 11/2017 | Luther et al. |
| 2018/0235692 A1 | 8/2018 | Efimov et al. |

OTHER PUBLICATIONS

Mette Funding la Cour, "Optical metabolic imaging of irradiated rat heart exposed to ischemia-reperfusion injury", Jan. 19, 2018 (Year: 2018).*

(Continued)

*Primary Examiner* — Maurice C Smith
(74) *Attorney, Agent, or Firm* — Blank Rome LLP

(57) ABSTRACT

A system and method for mapping metabolic data of a heart. The system has a light source directing light onto the heart, one or more lenses for focusing an image of the heart, and a fluorescent detector receiving the focused image and generating transients and/or waves to map metabolic cardiac data.

18 Claims, 4 Drawing Sheets

(56) References Cited

OTHER PUBLICATIONS

Matthew B. Bouchard, "Electrical and metabolic imaging of cardiac ischemia", 2008 (Year: 2008).*
Garry Papayan, "Autofluorescence spectroscopy for NADH and flavoproteins redox state monitoring in the isolated rat heart subjected toischemia-reperfusion", 2014 (Year: 2014).*
Huda Asfour, "NADH Fluorescence Imaging of Isolated Biventricular Working Rabbit Hearts", 2012 (Year: 2012).*
Cheri Deng, "Fluorescence Imaging for Real-Time Monitoring of High-Intensity Focused Ultrasound Cardiac Ablation", 2005 (Year: 2005).*
G. Schreier, "Noninvasive Patient Monitoring after Heart Transplantation—New Methodological Aspects", 1997 (Year: 1997).*
J. Kolarova, "Experimental Methods for Simultaneous Measurement of Action Potentials and Electrograms in Isolated Heart", 2010 (Year: 2010).*
Christopher O'Shea, "ElectroMap: High-throughput open-source software for analysis and mapping of cardiac electrophysiology", 2018 (Year: 2018).*
Fuhua Chen, "Effects of metabolic inhibition on conduction, Ca transients, and arrhythmia vulnerability in embryonic mouse hearts", Jul. 25, 2007 (Year: 2007).*
Mark R. Holcomb, The Potential of Dual Camera Systems for Multimodal Imaging of Cardiac Electrophysiology and Metabolism, Nov. 3, 2014 (Year: 2014).*
International Search Report & Written Opinion for PCT/US19/57769 dated Jan. 10, 2020, 16 pgs.
P. Kosterin, et al., "Changes in FAD and NADH Fluorescence in Neurosecretory Terminals are Triggered by Calcium Entry and by ADP Production", The Journal of Membrane Biology, vol. 208, Nos. 113-114, 2005, 12 pgs.
R. C. I. Wust, et al., "Rapid Changes in NADH and Flavin Autofluorescence in Rat Cardiac Trabeculae Reveal Large Mitochondrial Complex II Reserve Capacity", The Journal of Physiology, vol. 593.8, 2015, pp. 1829-1840.
EP Communication for EP Application No. 18748590.0, dated Dec. 12, 2020, 1 pg.
EP Search Report for EP Application No. 18748590.0, dated Nov. 12, 2020, 4 pgs.
Prof. Dr. Hyun-Joong Chung, et al., "Ultrathin, Stretchable, Multiplexing pH Sensor Arrays on Biomedical Devices with Demonstrations on Rabbitt and Human Hearts Undergoing Ischemia", Adv. Health Mater., Jan. 2014; vol. 3, No. 1, pp. 1-20.
L. Xu, et al., "3D Multifunctional Integumentary Membranes for Spatiotemporal Cardiac Measurements and Stimulation Across the Entire Epicardium", Nature Communications, www.nature.com/naturecommunications; Feb. 25, 2014; pp. 1-10.
L. Xu, et al., "Materials and Fractal Designs for 3D Multifunctional Integumentary Membranes with Capabilities in Cardiac Electrotherapy", Advanced Materials; www.MaterialsViews.com: 2015; vol. 27; pp. 1731-1737.
Dr. Ahyeon Koh, et al., "Ultrathin Injectable Sensors of Temperature, Thermal Conductivity, and Heat Capacity for Cardiac Ablation Monitoring", Adv. Healthc Mater., Feb. 4, 2016: vol. 5, No. 3, pp. 1-19.
H. Fang, et al., "Capacitively Coupled Arrays of Multiplexed Flexible Silicon Transistors for Long-Term Cardiac Electrophysiology", Nature Biomedical Engineering, www.nature.com/natbiomedeng; Mar. 2017; vol. 1, No. 0038; pp. 1-12.
J. G. McCall, et al., "Fabrication and Application of Flexible, Multimodal Light-Emitting Devices for Wireless Optogenetics", Nature Protocols; vol. 8, No. 12; Nov. 7, 2013; pp. 2413-2428.
S. P. Lee, et al., "Catheter-Based Systems with Integrated Stretchable Sensors and Conductors in Cardiac Electrophysiology", Proceedings of the IEEE, vol. 103, No. 4, Apr. 2015, pp. 682-669.

* cited by examiner

FAST LABEL-FREE METHOD FOR MAPPING CARDIAC PHYSIOLOGY

RELATED APPLICATIONS

This application claims the benefit of U.S. Provisional Application No. 62/749,937, filed Oct. 24, 2019, the entire contents of which are incorporated herein by reference.

GOVERNMENT LICENSE RIGHTS

This invention was made with Government support under Grant/Contract No. R01 HL126802 and R21EB023106 awarded by National Institutes of Health. The U.S. Government has certain rights in this invention.

BACKGROUND OF INVENTION

Field of the Invention

The present invention relates to label free fast cardiac mapping.

Background of the Related Art

NADH and FAD change their fluorescence properties on a beat-to-beat basis during metabolically normal states and during metabolically pathological states. Optical mapping can be used for various applications, such as for example, current clinical cardiac mapping techniques for the detection of arrhythmias and guiding ablation. Cardiac electrophysiology mapping is currently conducted in the clinic using multi-electrode arrays or a roving catheter approach.

Current optical mapping techniques provide high resolution spatio-temporal dynamics of cardiac physiology and arrhythmia using fluorescence probes designed for various physiological parameters, such as transmembrane potential, intracellular calcium, mitochondrial inner membrane potential, etc. However, they require perfusion-based staining with possibly toxic fluorescence probes, which precludes or limits their use in the clinical settings (Cheng, 1998). Alternatively, optical imaging of endogenous fluorophores, such as collagen, NADH (Nicotinamide adenine dinucleotide) and FAD (flavin-adenine dinucleotide) has been extensively utilized, but at a significantly slower temporal resolution (Chance, 1976; Salama, 1986; Wengrowski, 2013), which corresponds to seconds or minutes resolution and reflects slow metabolic impairment during ischemia, hypoxia and other pathological metabolic states developing over times scales of seconds or minutes. Metabolic spectroscopy single point studies in neurons and isolated rat pupillary muscle demonstrated that fluorescence corresponding to NADH and FAD changes at faster rates corresponding to beat-to-beat scales (Kosterin, 2005; Wust, 2015).

Current clinical methods for detecting and ablating sources of atrial or ventricular tachycardia or fibrillation rely on electrically sensitive catheters to map the electrical activity of the chambers of the heart. Electrically sensitive catheters have their drawbacks, including that they have relatively low resolution, rely on sequential probing areas of the heart with single probes, and the results of electrical probing are subjective to interpretation by the clinician.

SUMMARY OF THE INVENTION

A system and method for mapping metabolic data of a heart. The system has a light source directing light onto the heart, one or more lenses for focusing an image of the heart, and a fluorescent detector receiving the focused image and generating transients and/or waves to map metabolic cardiac data.

DETAILED DESCRIPTION OF THE INVENTION

Figure 1:
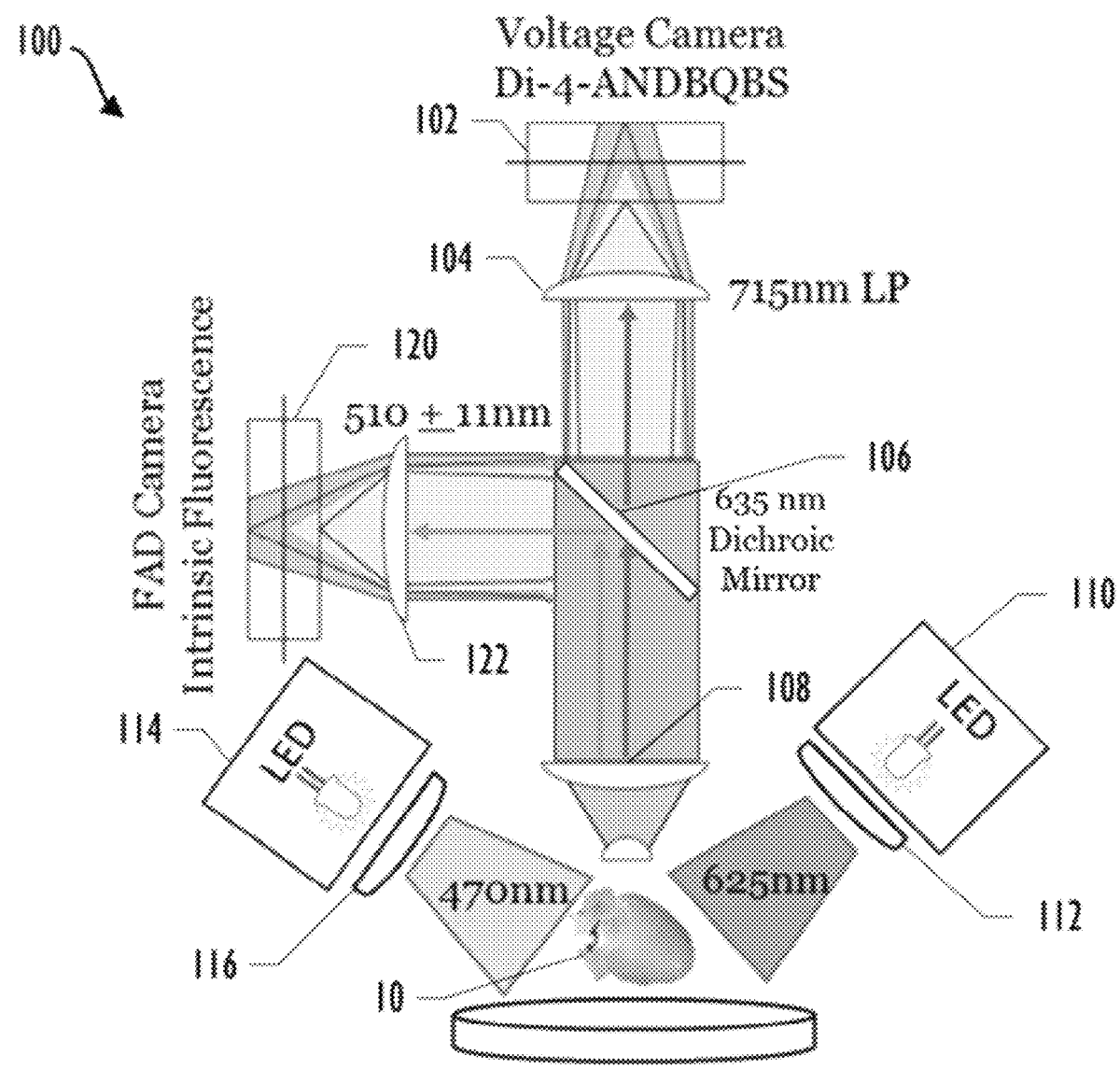
FIG. 1 is a block diagram of a mapping system in accordance with an embodiment of the invention.

In describing the illustrative, non-limiting embodiments of the invention illustrated in the drawings, specific terminology will be resorted to for the sake of clarity. However, the invention is not intended to be limited to the specific terms so selected, and it is to be understood that each specific term includes all technical equivalents that operate in similar manner to accomplish a similar purpose. Several embodiments of the invention are described for illustrative purposes, it being understood that the invention may be embodied in other forms not specifically shown in the drawings.

Turning to the drawings, FIG. 1 is a schematic of the dual optical mapping system 100 in accordance with an example non-limiting embodiment of the invention. The system 100 records excitation-metabolic waves at 1,000 frames per second. The system 100 includes a first imaging device 102, a first lens 104, a second imaging device 120, a second lens 122, a mirror 106, a third lens 108, one or more light emitting devices (LEDs) 110, 114, and respective light lenses 112, 116. The LEDs 110, 114 provide a light source, and the light lenses 112, 116 focus the light on the target 10, here a heart. One or more lenses 108 (here, two are shown) capture the image and focus it to the mirror 106. The mirror 106 allows the target image to pass through to the first imaging device 102 via the focusing lens 104. The mirror 106 also reflects the image to a second imaging device 120 via the second lens 122.

The two light sources 110, 114 excite voltage and fluorescence (e.g., FAD) at the same time. The dichroic mirror 106 separates the signals at a 45-degree angle. Voltage signals are detected by the first imaging device 102, such as for example by a voltage camera Di-4-ANDBQBS, with excitation at 625 nm and emission at 725 nm. FAD signals are intrinsically fluorescent (excitation at 470 nm and emission at 500-550 nm) and are captured by the second imaging device 120, such as for example by an FAD camera.

Figure 2:
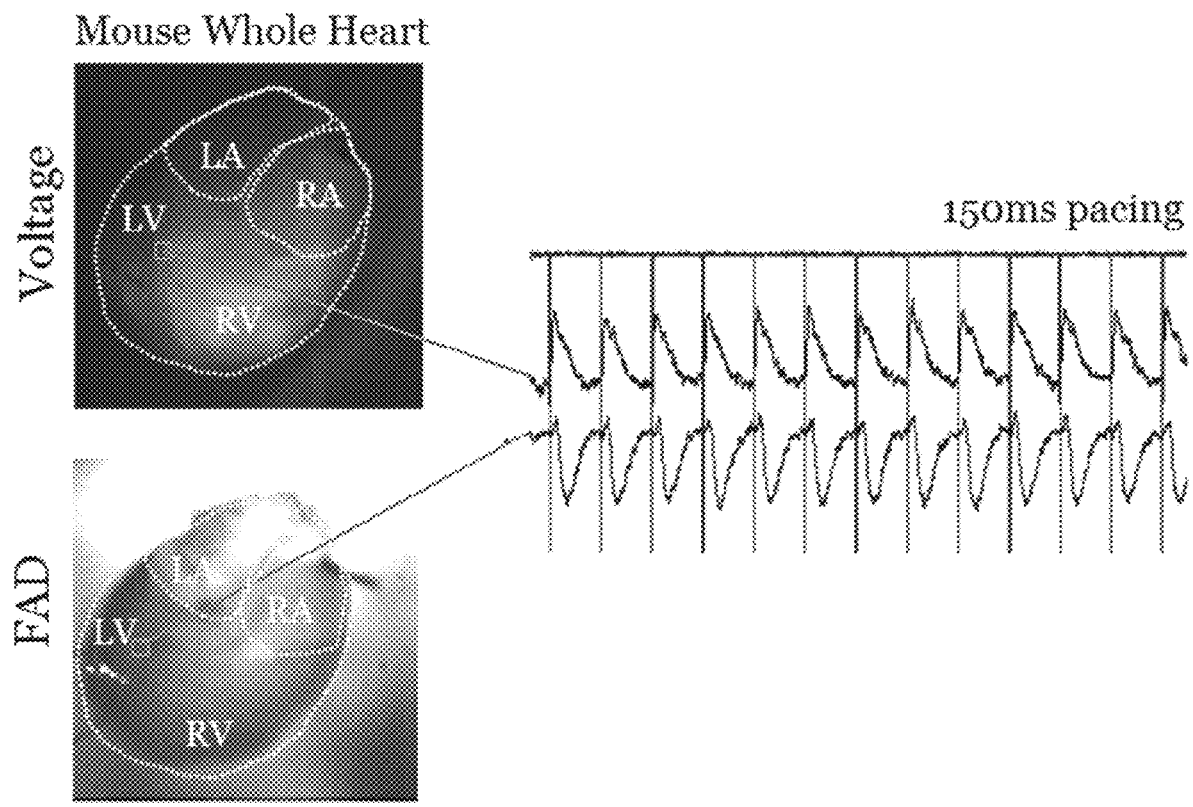
FIG. 2 is a graph of the voltage and FAD output for a mouse heart.

This configuration provides dual simultaneous fast optical mapping of voltage and FAD, for example in whole ex vivo mouse hearts. FIG. 2 shows metabolic FAD signals are opposite in direction to voltage signals in this case, showing the left atrium (LA), right atrium (RA), left ventricle (LV) and right ventricle (RV).

Figure 3:
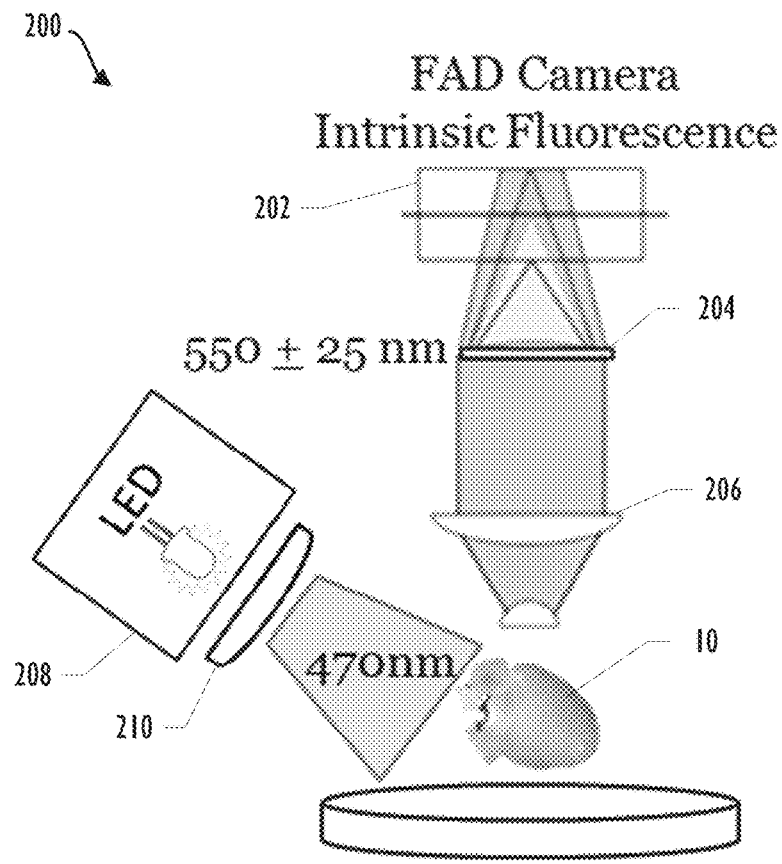
FIG. 3 is block diagram of an FAD mapping system in accordance with an embodiment of the invention.

FIG. 3 is a schematic of the optical mapping system 200 to acquire intrinsically fluorescent signals of FAD (excitation at 470 nm and emission at 525 nm). Specifically, the system 200 is used for optical label-free mapping of FAD in ex vivo isolated right atrial preparations of mouse and rat hearts. The system 200 includes an LEI) 208, focus lens 210, capture lens 206, lens 204, and imaging device 202. The LED 208 illuminates the target, here the heart 10, via lens 210. The image is picked up by one or more capture lenses 206 (here, two are shown), and passed to the lens 204, focuses the image to the camera 202, here an FAD camera that detects intrinsic fluorescence. Thus, FIG. 3 is another embodiment of fluorescence setup, which is simpler than that in FIG. 1. The system of FIG. 1 can be used to optically map two parameters (i.e. FAD and NADH) while the system of FIG. 3 can be used for imaging only one parameter (either FAD or NADH or other).

Figure 4:
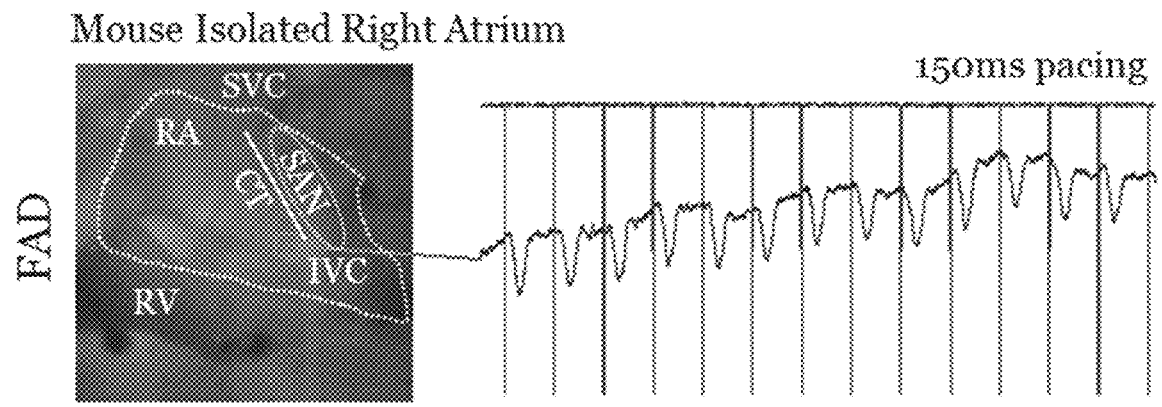
FIG. 4 is a graph of the fluorescence for the right atrium of a mouse heart.
Figure 5:
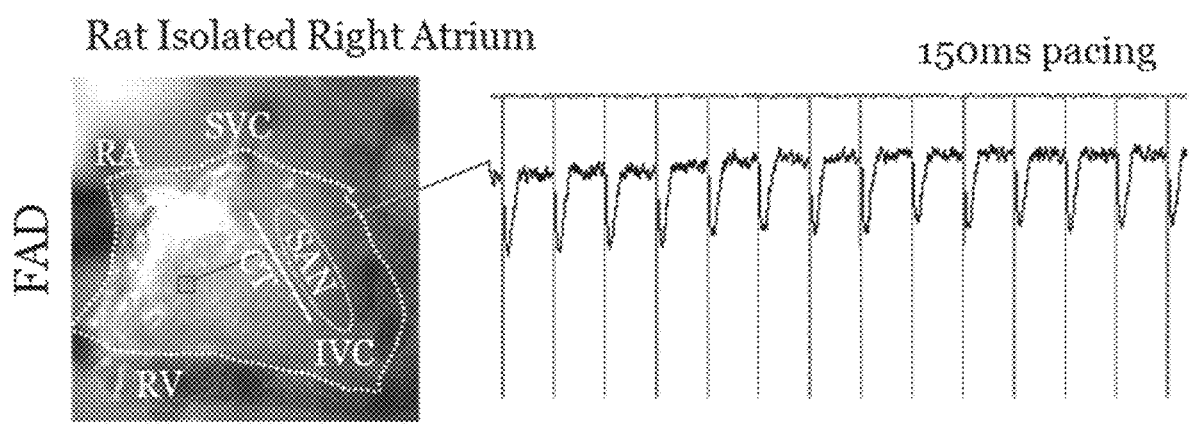
FIG. 5 is a graph of the fluorescence for the right atrium of a rat heart.

FIG. 4 shows label free recordings of FAD in the mouse isolated right atrium, and FIG. 5 shows label free recordings of FAD in the rat isolated right atrium. The metabolic FAD signals and their temporal dynamics can be measured on a beat-to-beat basis in both species, including the superior vena cava (SVC); crista terminalis (CT), sinoatrial node (SAN), and inferior vena cava (IVC).

Figure 6A:
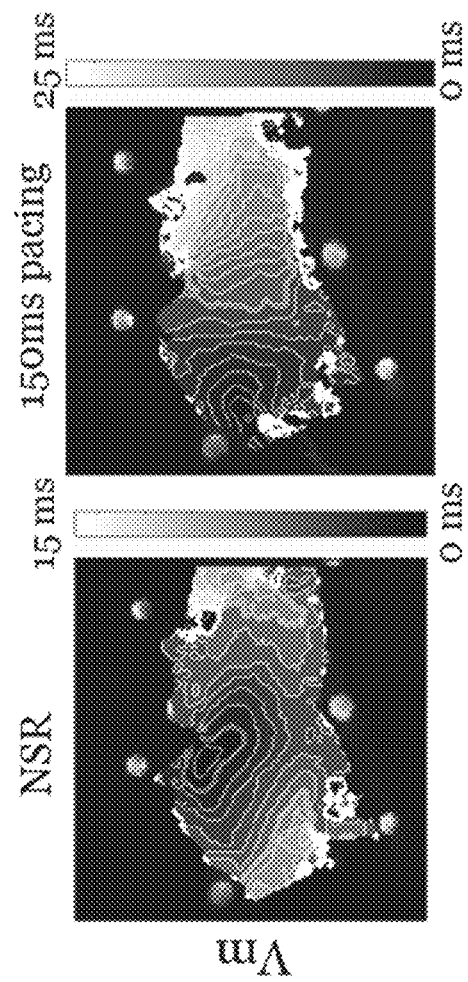
FIGS. 6A, 6B are optical label-free mapping of FAD and optical mapping of voltage in two ex vivo isolated right atrial preparations of rat hearts during normal sinus rhythm (NSR) and pacing (point stimulation).
Figure 6A:
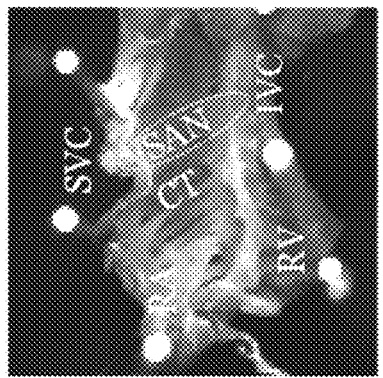
Figure 6B:
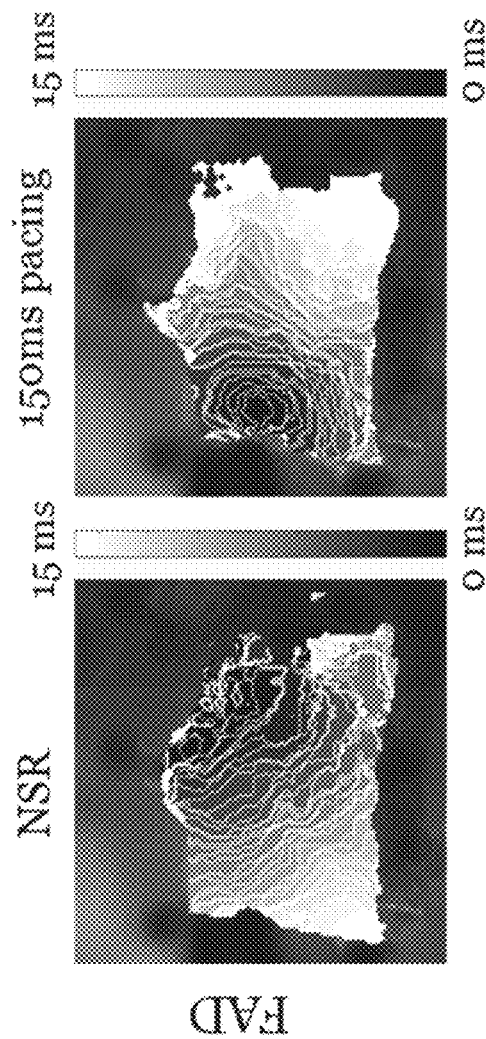
Figure 6B:
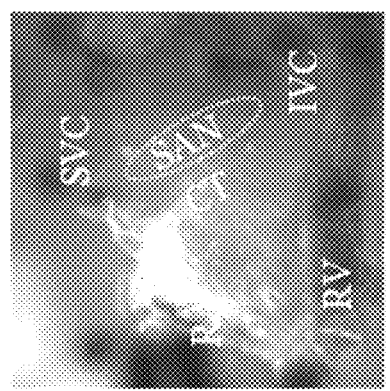

FIGS. 6A, 6B show optical label-free mapping of FAD and optical mapping of voltage in two ex vivo isolated right atrial preparations of rat hearts during normal sinus rhythm (NSR) and pacing (point stimulation). The left panels of FIGS. 6A, 6B show anatomical maps of rat atria which were mapped. The middle panel of FIG. 6A shows a map of initiation and propagation of transmembrane potential (6A) during normal sinus rhythm (NSR), also known as map of activation. This map was recorded using a voltage-sensitive dye. The middle panel of FIG. 6B shows label free map of initiation and propagation of FAD during normal sinus rhythm (NSR). Comparison of the two maps show good correlation of the two propagation processes which allows use of FAD map as a surrogate of map of activation. The right maps in FIGS. 6A, 6B show similar maps during electrical pacing from the free wall of the right atrium. Again, two maps show similar propagating processes initiating from the pacing site. Thus, metabolic map alone can help locate the source of ectopic activity or reentry during arrhythmia and guide the ablation procedure.

Accordingly, the invention presents a new method and system for fast label free optical mapping of spatio-temporal dynamics of cardiac electrophysiology and metabolism on a beat-to-beat basis, faster than 100 frames per second. The system 100, 200 eliminates the need for electrical catheters and for contrast agents needed for optical mapping of transmembrane potential. Such label free optical mapping is capable to provide high resolution maps of metabolic waves which follow electrical activation and therefore they can be used as surrogate of electrical mapping without requiring potentially toxic voltage-sensitive dye.

When recorded or mapped in spatio-temporal domain, these measurements provide real-time cardiac mapping. One advantage of the high spatial and temporal resolution mapping possibilities of this invention, for example for the detection of arrhythmias and guiding ablation, is that complex arrhythmia dynamic changes can be observed optically in the visible range, in real time, and with the ability to convey information on the relative health status of and physiological dynamics of the heart physiology, and to identify sources or drivers of arrhythmias and guide ablation procedure designed for elimination of these sources and treat the arrhythmia.

NADH and fluorescence (FAD) change their fluorescence on a beat-to-beat basis during metabolically normal states and during metabolically pathological states. Simultaneous fast mapping of NADH or FAD with voltage-sensitive or calcium-sensitive dyes demonstrates that an action potential is followed by a calcium transient and then by a metabolic transient. Fluorescence dyes or labels are used for mapping voltage and calcium, which makes their use doubtful in clinical settings due to potential cardiotoxicity. Metabolic waves of FAD and NADH do not require fluorescence dyes, because they are intrinsically fluorescent and can be optically mapped without any extrinsic labels. Thus, label-free fast mapping of metabolic transients/waves of the present invention can be used with or without electrical and calcium mapping, and can inform about the origin and propagation dynamics of excitation-contraction-metabolic waves during normal sinus rhythm, bradycardia, abnormal automaticity, pacing, resynchronization therapy, atrial and ventricular tachycardia, and atrial and ventricular fibrillation.

The present invention provides a fast label-free mapping system of excitation-contraction-metabolic waves at hundreds to thousands (e.g., 100-5,000) of frames per second in certain applications such as clinical and basic scientific applications. Such a system allows for clinical mapping of atrial and ventricular arrhythmia during, or prior to, ablation procedures to guide such procedures through the identification of the source/driver or sources/drivers of atrial tachycardia or fibrillation and of ventricular tachycardia or fibrillation. For example, FIG. 6B middle and right panel show driver of metabolic wave during normal sinus rhythm (NSR) and during pacing at 150 ms pacing cycle length, respectively. An intracardiac mapping system could be constructed in one embodiment with an organ conformal electronics platform equipped with multisite fluorescence electronic components comprising of a source of light (i.e. light guide coupled to an optical sensor, light emitting diode, etc.) and a sensor of light (i.e. photodiode, light guide coupled to an optical sensor, etc.). Dynamic mapping of waves of metabolism guide identification of pathological conduction or pathological initiation of activity within atria or ventricles to correct such pathology by ablation.

The system 100, 200 has a number of benefits and advantages. First, a fast label-free method for mapping cardiac physiology has the ability to better detect focal sources of arrhythmias as well as reentrant pathways with high spatio-temporal resolution. Second, this method and system is unique in that it can be stand-alone for cardiac electrical dysfunction detection purposes, but it can also be integrated onto an organ conformal electronics platform for simultaneous optical mapping and ablation purposes. Third, this system and method is free of labels, is non-toxic to the heart (and therefore the patient), and it capitalizes on the intrinsic fluorescence of metabolic signals. Fourth, metabolic waves are captured on a beat-to-beat basis, making this technology useful for readily replacing optical mapping of cardiac electrophysiology in experimental settings without the need for exogenous fluorescent dyes. Fifth, this system and method provides direct evaluation and informs about pathological metabolic states, which allows dynamic mapping of ischemic, hypoxic and other pathological metabolic events leading to electromechanical dysfunction and lethal arrhythmia and heart failure.

The system and method have been established in whole ex vivo mouse hearts (FIGS. 1-2), isolated mouse and rat atrial preparations (FIGS. 3-6), and is being tested ex vivo in human heart. Our spatio-temporal optical mapping recordings of metabolic transients are correlative with electrical conduction maps on a beat-to-beat basis. A small conformal device can be provided to quickly detect label-free metabolic waves of cardiac physiology over a wide range of mammalian hearts. For example, conformal devices are described in US20180235692A1, which is incorporated herein by reference. In addition, as described in US20180235692A1, an ablation catheter can be integrated within the same conformal flexible/stretchable bioelectronics device that will simultaneously sense and report the source or sources of tachycardia or fibrillation. In addition, an actuator can be provided to impart an electrical correction to the heart rhythm, such as an electrical pulse or shock.

The system and method of the present invention include operation by one or more processing devices, including to process data detected by the imaging devices 102, 120, and 202. The processing device can be any suitable device, such as a computer, server, mainframe, processor, microprocessor, PC, tablet, smartphone, or the like. The processing devices can be used in combination with other suitable components, such as a display device (monitor, LED screen, digital screen, etc.), memory or storage device, input device (touchscreen, keyboard, pointing device such as a mouse), wireless module (for RF, Bluetooth, infrared, WiFi, etc.). The information may be stored on a computer hard drive, on a CD ROM disk or on any other appropriate data storage device, which can be located at or in communication with the processing device. The entire process is conducted automatically by the processing device, and without any manual interaction. Accordingly, unless indicated otherwise the process can occur substantially in real-time without any delays or manual action. The invention can also be implemented on a medium, i.e., one or more non-transitory physical media that together store the contents described as being stored thereon. Embodiments may include non-volatile secondary storage, read-only memory (ROM), and/or random-access memory (RAM).

The foregoing description and drawings should be considered as illustrative only of the principles of the invention. The invention may be configured in a variety of shapes and sizes and is not intended to be limited by the embodiment. Numerous applications of the invention will readily occur to those skilled in the art. Therefore, it is not desired to limit the invention to the specific examples disclosed or the exact construction and operation shown and described. Rather, all suitable modifications and equivalents may be resorted to, falling within the scope of the invention.

The invention claimed is:

1. A system for mapping metabolic waves of a heart, comprising:
a light source directing light onto the heart;
one or more lenses for focusing an image of the heart; and
a fluorescent detector receiving the focused image at rates from 100 to 5,000 frames per second and generating transients and/or waves to map metabolic cardiac data, wherein the transients and/or waves are a visualization of an origin and propagation dynamics of excitation-contraction-metabolic waves representing heart arrhythmia.

2. The system of claim 1, wherein said fluorescent detector comprises a camera.

3. The system of claim 1, said system being label free.

4. The system of claim 1, said system being free of electrical and calcium mapping.

5. The system of claim 1, said transients and/or waves identifying normal sinus rhythm, bradycardia, abnormal automaticity, pacing, resynchronization therapy, atrial and ventricular tachycardia, and atrial and ventricular fibrillation.

6. The system of claim 1, wherein the light is at a wavelength of 470 nm.

7. A system for mapping metabolic waves of a heart, comprising:
a light source directing light onto the heart;
a fluorescent detector receiving the focused images at rates from 100 to 5,000 frames per second and generating transients and/or waves to map metabolic cardiac data, wherein the transients and/or waves are a visualization of an origin and propagation dynamics of excitation-contraction-metabolic waves representing heart arrhythmia.

8. The system of claim 7, wherein said fluorescent detector comprises a camera.

9. The system of claim 7, said system being label free.

10. The system of claim 7, said system being free of electrical and calcium mapping.

11. The system of claim 7, said transients and/or waves identifying normal sinus rhythm, bradycardia, abnormal automaticity, pacing, resynchronization therapy, atrial and ventricular tachycardia, and atrial and ventricular fibrillation.

12. The system of claim 7, wherein the light is at a wavelength of 470 nm.

13. A method for mapping metabolic waves of a heart, comprising:
directing light from a light source, onto the heart;
receiving, at a fluorescent detector, the focused images at rates from 100 to 5,000 frames per second and generating transients and/or waves to map metabolic cardiac data, wherein the transients and/or waves are a visualization of an origin and propagation dynamics of excitation-contraction-metabolic waves representing heart arrhythmia.

14. The method of claim 13, wherein the fluorescent detector comprises a camera.

15. The method of claim 13, said system being label free.

16. The method of claim 13, being free of electrical and calcium mapping.

17. The method of claim 13, the transients and/or waves identifying normal sinus rhythm, bradycardia, abnormal automaticity, pacing, resynchronization therapy, atrial and ventricular tachycardia, and atrial and ventricular fibrillation.

18. The method of claim 13, wherein the light is at a wavelength of 470 nm.

* * * * *